(12) United States Patent
Poland

(10) Patent No.: US 9,301,730 B2
(45) Date of Patent: Apr. 5, 2016

(54) ULTRASONIC DIAGNOSTIC IMAGING SYSTEM CONFIGURED BY PROBE FIRMWARE

(75) Inventor: McKee Dunn Poland, Andover, MA (US)

(73) Assignee: Koninklijke Philips N.V., Eindhoven (NL)

(*) Notice: Subject to any disclaimer, the term of this patent is extended or adjusted under 35 U.S.C. 154(b) by 2356 days.

(21) Appl. No.: 11/911,121

(22) PCT Filed: Mar. 31, 2006

(86) PCT No.: PCT/IB2006/050987
§ 371 (c)(1),
(2), (4) Date: Oct. 10, 2007

(87) PCT Pub. No.: WO2006/111873
PCT Pub. Date: Oct. 26, 2006

(65) Prior Publication Data
US 2008/0194951 A1    Aug. 14, 2008

Related U.S. Application Data

(60) Provisional application No. 60/672,630, filed on Apr. 18, 2005.

(51) Int. Cl.
*A61B 8/00* (2006.01)
*G01S 7/52* (2006.01)
*G01S 15/89* (2006.01)

(52) U.S. Cl.
CPC ............. *A61B 8/4405* (2013.01); *A61B 8/00* (2013.01); *A61B 8/4427* (2013.01); *A61B 8/4433* (2013.01); *G01S 7/52079* (2013.01); *G01S 15/899* (2013.01); *A61B 8/4411* (2013.01); *A61B 2560/0271* (2013.01); *A61B 2560/0456* (2013.01)

(58) Field of Classification Search
CPC ............... A61B 2560/0271; A61B 2560/0456; A61B 8/00; A61B 8/4405; A61B 8/4411; A61B 8/4427; A61B 8/4433; G01S 15/899; G01S 7/52079
See application file for complete search history.

(56) References Cited

U.S. PATENT DOCUMENTS

| | | | |
|---|---|---|---|
| 4,868,476 A | 9/1989 | Respaut | |
| 5,590,658 A * | 1/1997 | Chiang et al. | 600/447 |
| 5,603,323 A | 2/1997 | Pflugrath | |
| 5,997,479 A | 12/1999 | Savord | |
| 6,364,839 B1 * | 4/2002 | Little et al. | 600/459 |
| 6,375,617 B1 | 4/2002 | Fraser | |
| 6,475,146 B1 | 11/2002 | Frelburger | |
| 6,491,634 B1 * | 12/2002 | Leavitt et al. | 600/447 |
| 6,500,120 B1 * | 12/2002 | Anthony | 600/437 |

(Continued)

FOREIGN PATENT DOCUMENTS

| | | |
|---|---|---|
| JP | 2003010180 | 1/2003 |
| JP | 2004229979 | 8/2004 |
| WO | 9701768 | 1/1997 |

*Primary Examiner* — Michael Rozanski

(57) ABSTRACT

An ultrasonic diagnostic imaging system (50) includes analog and/or digital components which are configurable by firmware data. An ultrasound probe (10) contains firmware data for configuring the programmable devices of an ultrasound system for operation with the probe. The firmware data is uploaded from the probe and used to configure the analog and/or digital components for operation with the probe at runtime.

17 Claims, 5 Drawing Sheets

(56) References Cited

U.S. PATENT DOCUMENTS

| | | | |
|---|---|---|---|
| 6,524,244 B1* | 2/2003 | Knell et al. | 600/437 |
| 6,638,226 B2* | 10/2003 | He et al. | 600/443 |
| 6,638,228 B1* | 10/2003 | Brock-Fisher et al. | 600/443 |
| 6,669,633 B2* | 12/2003 | Brodsky et al. | 600/437 |
| 6,676,600 B1 | 1/2004 | Conero | |
| 6,783,493 B2* | 8/2004 | Chiang et al. | 600/437 |
| 6,827,686 B2* | 12/2004 | Szabo et al. | 600/458 |
| 6,969,352 B2* | 11/2005 | Chiang et al. | 600/437 |
| 6,969,353 B2* | 11/2005 | Brock-Fisher et al. | 600/458 |
| 7,141,020 B2* | 11/2006 | Poland et al. | 600/447 |
| 2002/0067359 A1* | 6/2002 | Brodsky et al. | 345/440 |
| 2002/0120193 A1* | 8/2002 | Chiang et al. | 600/439 |
| 2003/0073894 A1* | 4/2003 | Chiang et al. | 600/407 |
| 2003/0088182 A1* | 5/2003 | He et al. | 600/446 |
| 2003/0100833 A1* | 5/2003 | He et al. | 600/446 |
| 2003/0158482 A1* | 8/2003 | Poland et al. | 600/446 |
| 2003/0204142 A1* | 10/2003 | Brock-Fisher et al. | 600/458 |
| 2004/0002657 A1* | 1/2004 | Marian | 600/459 |
| 2004/0002658 A1 | 1/2004 | Marian | |
| 2004/0015079 A1* | 1/2004 | Berger et al. | 600/437 |
| 2004/0030253 A1* | 2/2004 | Brock-Fisher et al. | 600/458 |
| 2004/0039282 A1* | 2/2004 | Szabo et al. | 600/437 |
| 2004/0220475 A1* | 11/2004 | Szabo et al. | 600/458 |
| 2005/0251035 A1* | 11/2005 | Wong et al. | 600/437 |
| 2006/0264746 A1* | 11/2006 | Frisa et al. | 600/437 |

* cited by examiner

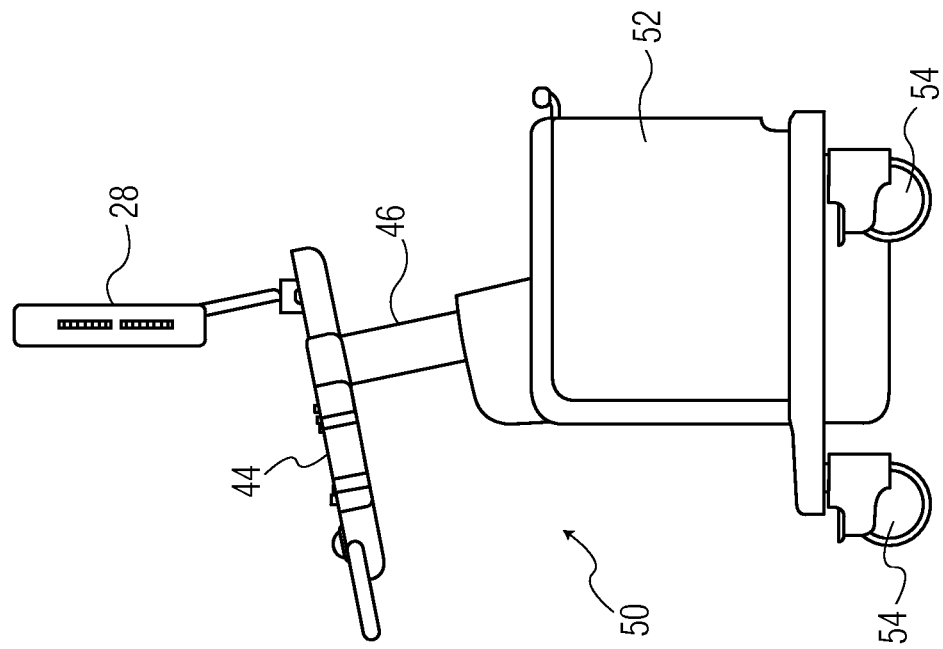
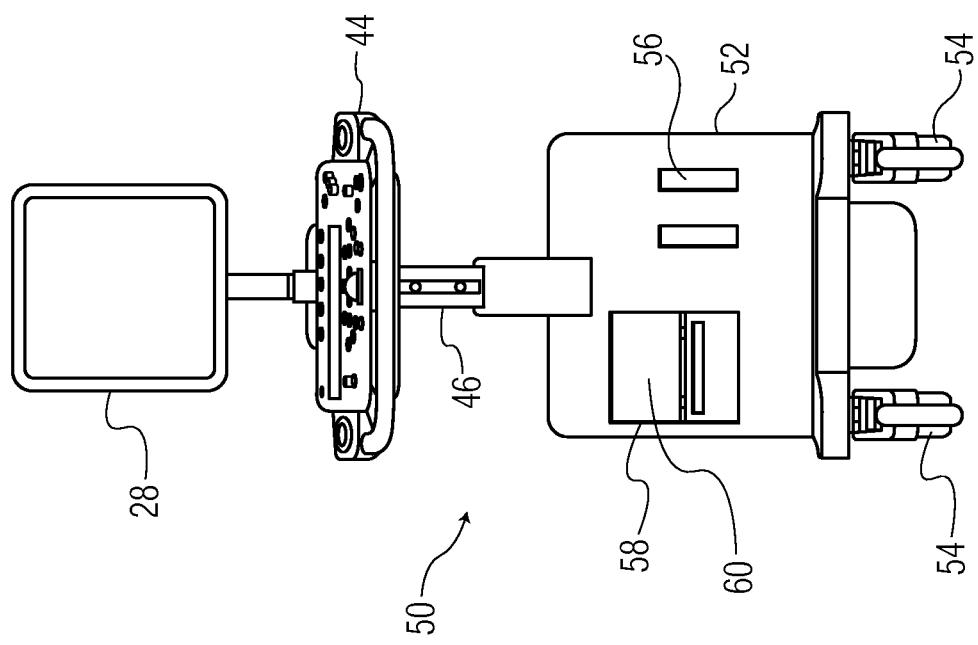

ULTRASONIC DIAGNOSTIC IMAGING SYSTEM CONFIGURED BY PROBE FIRMWARE

This invention relates to ultrasonic diagnostic imaging systems and, in particular, to ultrasound systems with processing architecture configurable by firmware stored in the ultrasound probe.

The versatility of a diagnostic ultrasound system is largely determined by the types of probes which can be used with the system. Linear array transducer probes are generally preferred for abdominal and small parts imaging and phased array transducer probes are preferred for cardiac imaging. Probes may have 1D or 2D array transducers for two dimensional or three dimensional imaging. Indwelling probes such as IVT and TEE probes are in common use, as are specialty probes such as surgical probes. Each type of probe can operate at a unique frequency range and have a unique aperture and array element count. Some probes are designed for grayscale operation or operation at the transmit frequency while others can perform color Doppler imaging or harmonic imaging. This variation in probe characteristics and functionality means that the processing system operable with a variety of probes must be reprogrammed each time a different probe is put to use. Traditionally this has been done by installing probe-specific software each time an ultrasound system is to operate with a new probe. Sometimes probe software is installed in advance of a user's acquisition of the new probe. The software for a full complement of current probes can be loaded when a system software upgrade is performed, for instance. Both of these approaches have required a visit by an ultrasound system technician, however. The need for a visit by a serviceperson began to be eliminated when the ability to install ultrasound system software from a remote location was developed, as described in U.S. Pat. No. 5,603,323 (Pflugrath et al.) With this advance networks such as the Internet enabled a serviceperson to install new probe software without having to travel to the site of the ultrasound system.

For many years probes have included their own onboard software such as the transducer drive and power requirement data stored in the EPROM of the probe connector. When the probe is connected to the ultrasound system, the system accesses this data through the probe connector and sets up the system transmitter to drive the probe transducer elements with appropriate voltages. See U.S. Pat. No. 4,868,476 (Respaut). In recent years probes have been developed with their own onboard integrated circuit processors as shown in U.S. Pat. No. 6,375,617 (Fraser et al.) and U.S. Pat. No. 5,997,479 (Savord et al.) Onboard IC processors are virtually essential for 2D matrix array probes, which otherwise would present challenges such as overly sized probe cables and beamformers with very large channel counts. The presence of IC power availability and communication capability in probes and their connectors, and the decreasing size and cost of memory devices, have made probe storage of an everexpanding range of software a practical expedient. For instance U.S. Pat. No. 6,364,839 (Little et al.) proposes to store operational software and updates and upgrades of system executable code in a memory device in the probe connector. US Pat. appl. pub. no. 2004/0002657 (Marian) expands this list to include transducer usage data, user comments, technical support, and maintenance data of the probe. The gigabyte sizes of today's memory devices have made it possible to store all of the software of a new probe software upgrade in the probe connector, from which the system can upload and install it when the probe is connected to the ultrasound system.

The use of such onboard probe software does impose constraints on the ultrasound system, however. The ultrasound system must be designed to accept this software and be capable of uploading and properly installing the software. Moreover, the ultrasound system must have fixed hardware which is designed to be programmed by the probe software. If the ultrasound system beamformer utilizes delay table data, the probe must contain delay data in the required tabular format. But if the system beamformer uses runtime algorithms to generate beamformer delay values, the probe software must have the required algorithmic format. The fixed hardware of the ultrasound system mandates and limits the nature of the software carried by the probe and the probe, in turn, is only operable with systems having hardware designed to accept and utilize their onboard software.

In accordance with the principles of the present invention, an ultrasound probe contains firmware which is used to configure the system for operation with the probe. Unlike conventional software, which provides parameters that initialize or control the operation of an existing hardware architecture or programs that run on an existing processor, the probe firmware actually defines hardware architectural features such as connections between components and their layout. The firmware stored in the probe is accessed and used to define a hardware architecture that operates with the probe such as the functionality of a field programmable gate array or programmable analog device. This capability means that the ultrasound system can be produced in a form in which it is nonspecific for any particular probe, taking on its specific hardware characteristics after being programmed by the firmware of the probe.

In the drawings:

FIGS. 2a and 2b illustrate a cart-like docking station for the system of FIG. 1.

Figure 1:
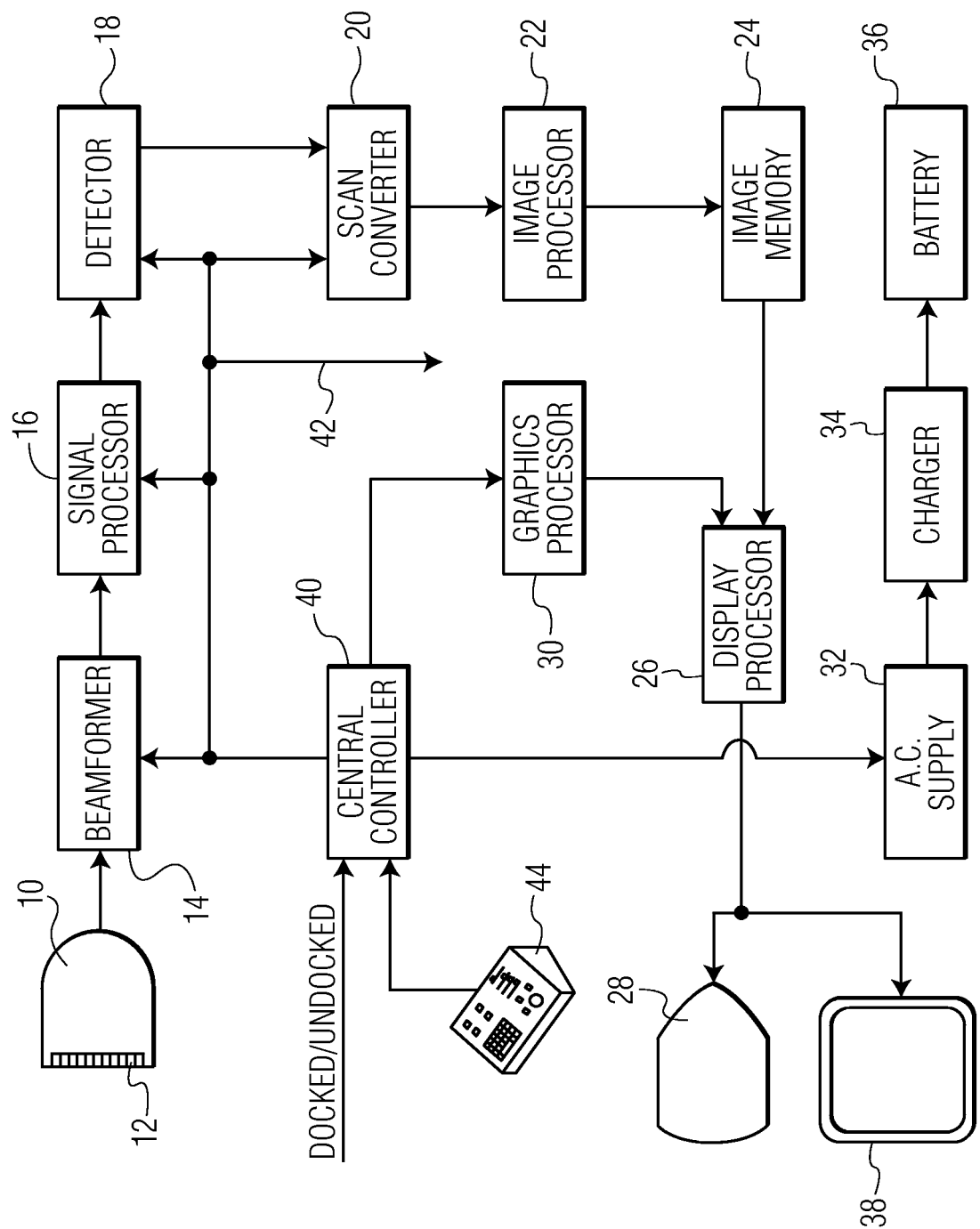
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. An ultrasound probe 10 transmits and receives ultrasound waves from the piezoelectric elements of an array of transducer elements 12. For imaging a planar region of the body a one-dimensional (1-D) array of elements may be used, and for imaging a volumetric region of the body a two-dimensional (2-D) array of elements may be used to steer and focus ultrasound beams over the image region. A transmit beamformer actuates elements of the array to transmit ultrasound waves into the subject. The signals produced in response to the reception of ultrasound waves are coupled to a receive beamformer 14. The beamformer delays and combines the signals from the individual transducer elements to form coherent beamformed echo signals. When the probe includes a 2-D array for 3D imaging, it may also include a microbeamformer which does partial beamforming in the probe by combining signals from a related group ("patch") of transducer elements as described in U.S. Pat. No. 6,709,394. In that case the microbeamformed signals are coupled to the main beamformer 14 in the system which completes the beamforming process.

The beamformed echo signals are coupled to a signal processor 16 which processes the signals in accordance with the information desired. The signals may be filtered, for instance, and/or harmonic signals may be separated out for processing. The processed signals are coupled to a detector 18 which detects the information of interest. For B mode imaging amplitude detection is usually employed, whereas for spectral and color Doppler imaging the Doppler shift or frequency can be detected. The detected signals are coupled to a scan converter 20 where the signals are coordinated to the desired display format, generally in a Cartesian coordinate system. Common display formats used are sector, rectilinear, and parallelogram display formats. The scan converted signals are coupled to an image processor for further desired enhancement such as persistence processing. The scan converter may be bypassed for some image processing. For example the scan converter may be bypassed when 3D image data is volume rendered by the image processor by direct operation on a 3D data set. The resulting two dimensional or three dimensional image is stored temporarily in an image memory 24, from which it is coupled to a display processor 26. The display processor produces the necessary drive signals to display the image on a docking station image display 28 or the flat panel display 38 of the portable system. The display processor also overlays the ultrasound image with graphical information from a graphics processor 30 such as system configuration and operating information, patient identification data, and the time and date of the acquisition of the image.

A central controller 40 responds to user input from the user interface and coordinates the operation of the various parts of the ultrasound system, as indicted by the arrows drawn from the central controller to the beamformer 14, the signal processor 16, the detector 18, and the scan converter 20, and the arrow 42 indicating connections to the other parts of the system. The user control panel 44 is shown coupled to the central controller 40 by which the operator enters commands and settings for response by the central controller. The central controller 40 is also coupled to an a.c. power supply 32 to cause the a.c. supply to power a battery charger 34 which charges the battery 36 of the portable ultrasound system when the portable system is docked in the docking station.

The central controller 40 is also responsive to a signal indicating whether the portable ultrasound system is docked or undocked, as indicated by the "Docked/Undocked" input to the central controller. This signal can be supplied by the operator pressing a Docked/Undocked button, a switch which changes state when the portable system is docked or undocked, or other suitable sensor of the docked/undocked condition. When the central controller is informed that the portable ultrasound system is docked in the docking station, the central controller responds to inputs from the user control panel 44, and causes the image to be displayed on the docking station display 28. The central controller also controls the graphics processor 30 during docking to omit the display of any softkey controls which duplicate the control functions of controls on the user control panel 44. The central controller may command the a.c. supply 32 and charger 34 to charge the battery 36 when the portable ultrasound system is docked, and/or power the docked portable system from a power supply on the docking station.

When the central controller is informed that the portable ultrasound system is undocked, these control characteristics are different. The controller now knows that user commands will not be received from the docking station control panel 44. The controller now causes some or all of the controls of the control panel 44 to be displayed when needed on the portable system display 38, as well as the ultrasound images produced by the ultrasound signal path. The a.c. supply 32 and the charger 34 are no longer controlled, as those subsystems are resident on the docking station. Probes will now be controlled through a probe connector on the portable system rather than through connectors on the docking station. The portable ultrasound system is now fully operable as a stand-alone ultrasound system.

It is thus seen that, in this embodiment, the partitioning of the components of FIG. 1 is as follows. The central controller 40, beamformer 14, signal processor 16, detector 18, scan converter 20, image processor 22, image memory 24, display processor 26, graphics processor 30, flat panel display 38, and battery 36 reside in the portable ultrasound system. The control panel 44, display 28, a.c. supply 32 and charger 34 reside on the docking station. In other embodiments the partitioning of these subsystems may be done in other ways as design objectives dictate.

FIGS. 2a and 2b illustrate a docking station 50 constructed in accordance with the principles of the present invention. This docking station 50 greatly resembles a conventional cart-borne ultrasound system with a base unit 52 supporting the user control panel 44 on an adjustable support 46 which enables the control panel to be raised or lowered to accommodate the comfort of different users. The docking station display 28 is mounted above the control panel 44, preferably on an adjustable support. An articulating adjustable support which serves this purpose is described in U.S. patent application Ser. No. 60/542,893 and international application no. PCT/IB2005/050405. The base unit 52 houses peripheral devices which the ultrasound system may use such as a printer, disk drive, and video recorder. The docking station 50 can be rolled to an exam room or patient bedside on wheels 54. The base unit also houses the a.c. supply 32 and battery charger 34. The base unit may also have connections to connect the ultrasound system to a data network.

Figure 2C:
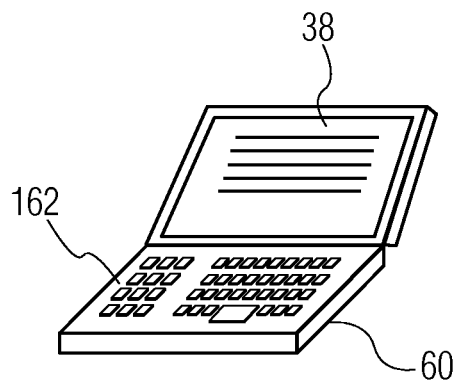
FIG. 2c illustrates a portable ultrasound system of the present invention which is suitable for use with the docking station of FIGS. 2a and 2b.

The base unit 52 has an enclosure 58 in the front into which a portable ultrasound system 60 can be located. A typical portable ultrasound system 60 is shown in FIG. 2c which in this embodiment is configured as a laptop PC with a screen 38 and a keyboard 62. In other embodiments the portable ultrasound system could be configured as a notebook or tablet PC with a screen surrounded by only a few buttons; the majority of the user interface is softkeys on the display screen. When the portable ultrasound system 60 is inserted into enclosure 58 a connector on the portable system 60 engages a mating connector of the docking station. It is this engagement which, directly or indirectly, results in the "Docked" control signal being delivered to the central controller 40 of the portable system. The connector also provides the necessary connections to the control panel 44, the display 28, and the a.c. supply 32, as well as the connection of the portable system battery 36 to the charger 34. This connector or another connector may also connect the portable system to one or more probe connectors 56 on the docking station. Alternatively, the probes may be connected to the portable system directly as they are in the portable mode, as by an opening on the side of the base unit 52 which permits the probe connector to engage the portable system 60.

Figure 3:
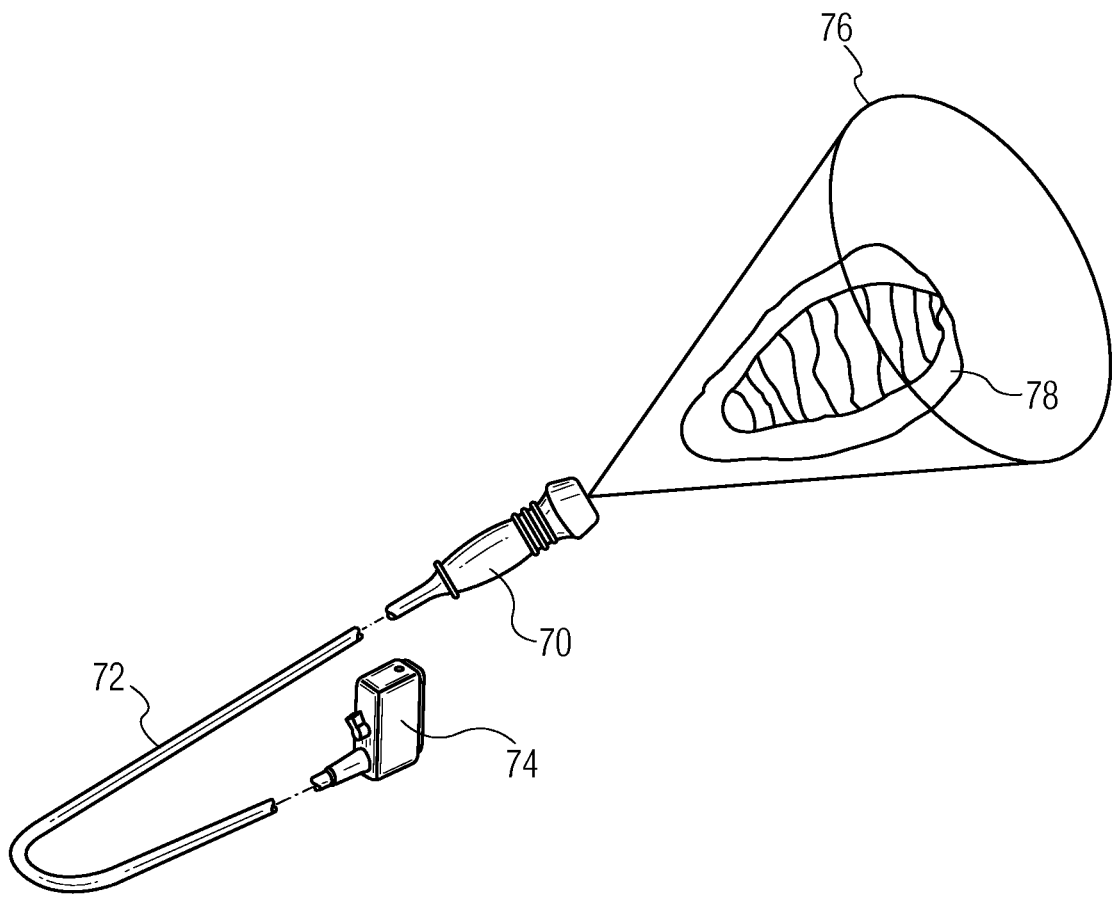
FIG. 3 illustrates a three dimensional imaging probe and connector.

In one embodiment of the present invention the ultrasound probe comprises a matrix array probe as described in U.S. Pat. No. 6,375,617 (Fraser et al.) and U.S. Pat. No. 5,997,479 (Savord et al.) A matrix array probe is shown in FIG. 3, and includes a probe body 70 which contains the two dimensional array transducer, a cable 72 and a connector 74 which mates with a connector on the ultrasound system such as a connector 56. The matrix array probe is capable of scanning a volumetric region such as conical region 76 which in this illustration contains anatomy 78. The matrix array probe contains not only a transducer array but also microbeamformer circuitry which performs at least some of the beamforming of the signals received by the probe. A matrix array probe can also make efficient and compact use of a two-dimensional array transducer which can perform three dimensional imaging, either images of a volumetric region or of several planes occupying a volumetric region. When some of the beamforming is performed in the probe, a reduced processing burden is imposed on the ultrasound system to which the matrix probe is connected and operates.

When the portable ultrasound system is configured from a standard portable PC such as a laptop or notebook PC a number of advantages can be obtained. One of the advantages that is usually obtained is cost. By taking advantage of the processing power and existing packaging of a laptop PC as shown in FIG. 2c, for example, no specialized packaging components are needed, reducing the cost of the portable system. Much of the signal processing and all of the display processing and user interface control can be performed using the microprocessor(s) of the portable PC unit and its associated components such as RAM, its network and peripheral connections, and disk drive. The power supply of the portable PC unit can power the entire portable ultrasound system including the ultrasound probe. Images can be displayed on the flat panel display 38 of the portable PC unit 60, as well as softkeys for the user interface. The keyboard and pointing device of the standard PC unit controls can be adapted to control the portable ultrasound system. In addition, connectors for interfacing laptop PCs to docking stations are well developed and commercially available, reducing that cost of system development. When realized in a laptop PC package use can be made of the conventional keyboard and controls 62 of the laptop PC including the touchpad or joystick pointing device commonly integrated into the laptop keyboard. The portable ultrasound system display 38 is provided by the conventional flat panel display 38 of the laptop PC, which can be modified to be at least partly or wholly a touchscreen display.

Figure 4:
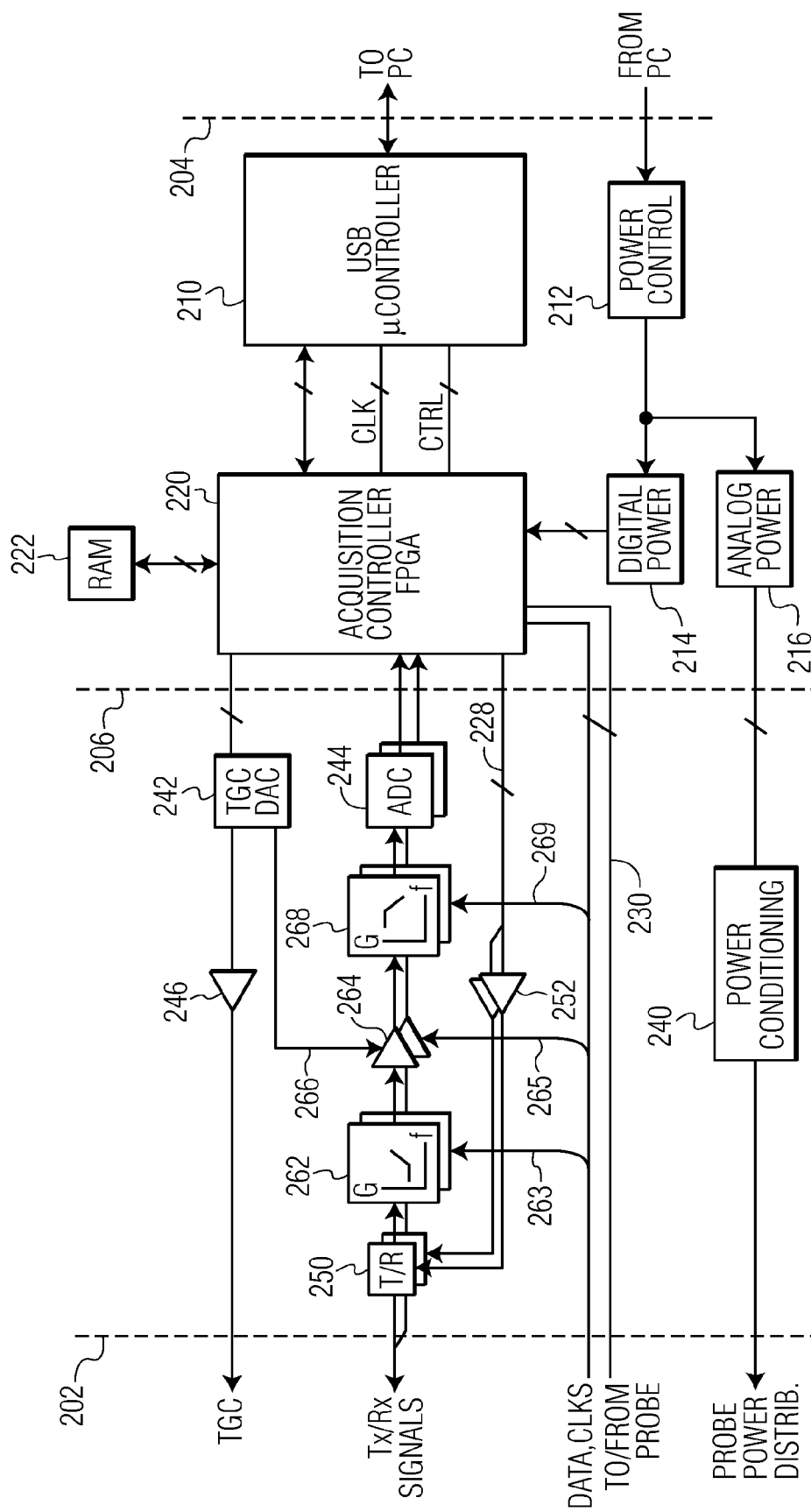
FIG. 4 illustrates in block diagram form the acquisition subsystem of a portable ultrasound system constructed in accordance with the principles of the present invention.

Another advantage of laptop or notebook PC packaging for the portable ultrasound system is the convenience of interfacing to a matrix array or 1D array probe. FIG. 4 illustrates a first such interface in block diagram form. In this embodiment the interface comprises the ultrasound acquisition portion of the ultrasound system following the microbeamformer and is constructed in accordance with the principles of the present invention. Rather than be constructed as a fixed hardware configuration this acquisition subsystem is composed of programmable analog and digital hardware, the configuration of which is determined by firmware provided by the probe. Prior to being configured this hardware may be an unassociated collection of components or modules which do not yet function as an ultrasound subsystem. In an FPGA, for example, these components and modules may be devices such as logic gates, multiplexers, adders, counters, multiplexers, memory devices, FIFOs and FIR filters, components which can find utility in an ultrasound system. When configured with firmware from the probe the generalized hardware takes on an ultrasound system character as components are interconnected, laid out, and clocked so as to become the ultrasound subsystem needed by the probe. Reduced power consumption can be attained by the firmware configuration process which needs to assemble only those components needed for an ultrasound subsystem for the particular probe, a significant consideration for a portable ultrasound system. The firmware configuration of the hardware can be done as late as runtime, when the programmable components are actually being called on to perform ultrasound functions.

In the illustration of FIG. 4 the ultrasound acquisition subsystem comprises both programmable analog hardware and programmable digital hardware. The dashed line 202 to the left marks the interface of the programmable acquisition subsystem to a probe such as a matrix array probe. The dashed line 204 on the right marks the interface of the acquisition subsystem to the processor of a portable PC. In this embodiment the interface to the PC comprises a USB connection although a serial connection such as a PCMCIA interface can also be employed. In the embodiment of FIG. 4 the PC interface is connected to the standard lines of a USB connection, including the USB serial data line and the USB DC (power) line shown to the right of dashed line 204. Thus, the ultrasound probe in this embodiment is interfaced to the portable PC by a standard USB interface, reducing the cost and complexity of the interface to the PC as compared to a specialized, nonstandard interface.

The probe-PC interface can be divided into two types of circuitry. The circuitry between dashed lines 204-206 is predominately digital circuitry which may, if desired, be fabricated as a digital circuitry module. The region between dashed lines 202-206 is predominately a region of analog circuitry which may, if desired, be fabricated as an analog circuitry module. Alternately, both modules may be fabricated on a common printed circuit board. Such a board or boards can conveniently be located in a standard laptop PC compartment such as the extra battery or disk drive bay. Thus, the interface can be realized as modules which are located inside the case of the laptop PC rather than as a separate module box that is used between the probe and the portable PC.

In this embodiment the illustrated acquisition circuitry communicates with the microprocessor of the portable ultrasound system by a USB interface. In other embodiments a parallel data interface such as a PCMCIA interface can be used as shown in concurrently filed U.S. Provisional Pat. App. Ser. No. 60/672,631, entitled "PC-BASED PORTABLE ULTRASONIC DIAGNOSTIC IMAGING SYSTEM." The USB DC lines are coupled to power control circuitry 212 which distributes DC power to digital power circuitry 214 and analog power circuitry 216. The digital power circuitry 214 distributes power to the digital components of the digital module including, in this embodiment, a USB microcontroller 210 and an acquisition controller FPGA (field programmable gate array) 220 and its accessory components such as RAM 222. The USB microcontroller 210 exchanges USB data with the portable system PC over the USB data line and with the FPGA 220 over data, clock and control lines. The USB microcontroller is the means by which the FPGA and the portable PC communicate through a USB port. The acquisition controller FPGA is a programmable hardware device that performs most or all of the ultrasound acquisition functions of the portable ultrasound system, such as transmit and receive beamforming, filtering, demodulation, harmonic separation and, if desired and given sufficient FPGA circuitry, amplitude and/or Doppler detection. In accordance with the principles of the present invention the FPGA 220 is programmed by firmware provided by the probe to provide some or all of these functions in a form which is compatible with the probe.

In the analog module the analog power circuitry 216 of the digital module is coupled to power conditioning circuitry 240 which distributes power to the components of the analog module and is also connected to provide power to the power distribution circuitry of the probe. The FPGA 220 provides beamformer data and clock signals for the microbeamformer of the matrix array probe on lines 230. In this embodiment these lines pass through the analog module for connection to the probe. Bipolar drive signals for the transducer elements of the probe are provided by the FPGA 220 on lines 228, amplified by amplifiers 252, and coupled to the probe by transmit/receive switches 250. Ultrasound signals received by the transducer elements of the probe are microbeamformed and amplified in the probe, then coupled through the transmit/receive switches 250 to programmable analog circuits of the analog module. The received signals first pass through programmable harmonic filters 262 which are programmed by a frequency control signal on line 263 from the probe. When the probe is receiving signals in a harmonic band of the transmit frequency such as a second harmonic band, the harmonic filters 262 are programmed to have a cutoff above the fundamental frequency band as illustrated by the response characteristic in the drawing. When fundamental frequency imaging is to be performed the harmonic filters are programmed to pass the fundamental frequencies of the received echo signals.

The signals are coupled to another set of programmable analog components, variable gain amplifiers 264. The gain of these amplifiers is controlled in part by a gain control signal on line 265 from the probe. The gain of these amplifiers is also controlled by a TGC gain control signal on line 266 which is set by a digital TGC signal from the FPGA which is converted to analog form by a TGC DAC 242. The amplified signals are coupled to a programmable anti-aliasing (Nyquist) filter set 268. These filters are programmed to have a cutoff by a frequency control signal from the probe on line 269 which attenuates higher frequency signals which would otherwise undesirably appear in the digitized echo signals. This cutoff is determined by the frequencies of the desired echo signals and the programmable sampling rate of ADCs 244. The echo signals are digitized by analog to digital converters 244 and coupled to the FPGA 220.

Analog components which are suitable for use in an embodiment of the present invention include Cypress Semiconductor's pSoC component family. Reconfigurable analog hardware enables the system circuitry to be configured to meet the needs of a specific probe. For instance the cutoff frequencies of an analog filter can be matched to the resonant frequencies and bandwidths of the transducer elements. Analog gain can be matched to the sensitivity of the probe elements. Trade-offs can be made between the signal-to-noise ratio of the front end circuitry and dynamic range. Hardware can be used for different purposes on different probes. For instance, a bandpass filter for one probe can be reconfigured as a Nyquist filter for another probe. There is no need to have two such circuits in the system all of the time as a fixed hardware configuration would require. Thus, unneeded circuitry is eliminated, reducing power consumption.

In this embodiment TGC control is partitioned and applied at various points in the signal path. In addition to the TGC control applied to variable gain amplifiers 264, TGC control is also effected by a second TGC signal produced by TGC DAC 242. This TGC signal is amplified by amplifier 246 and coupled to the probe microbeamformer where it is used in preliminary amplification of received echo signals in the probe. A portion of the TGC control is also performed digitally in the FPGA 220.

Figure 5:
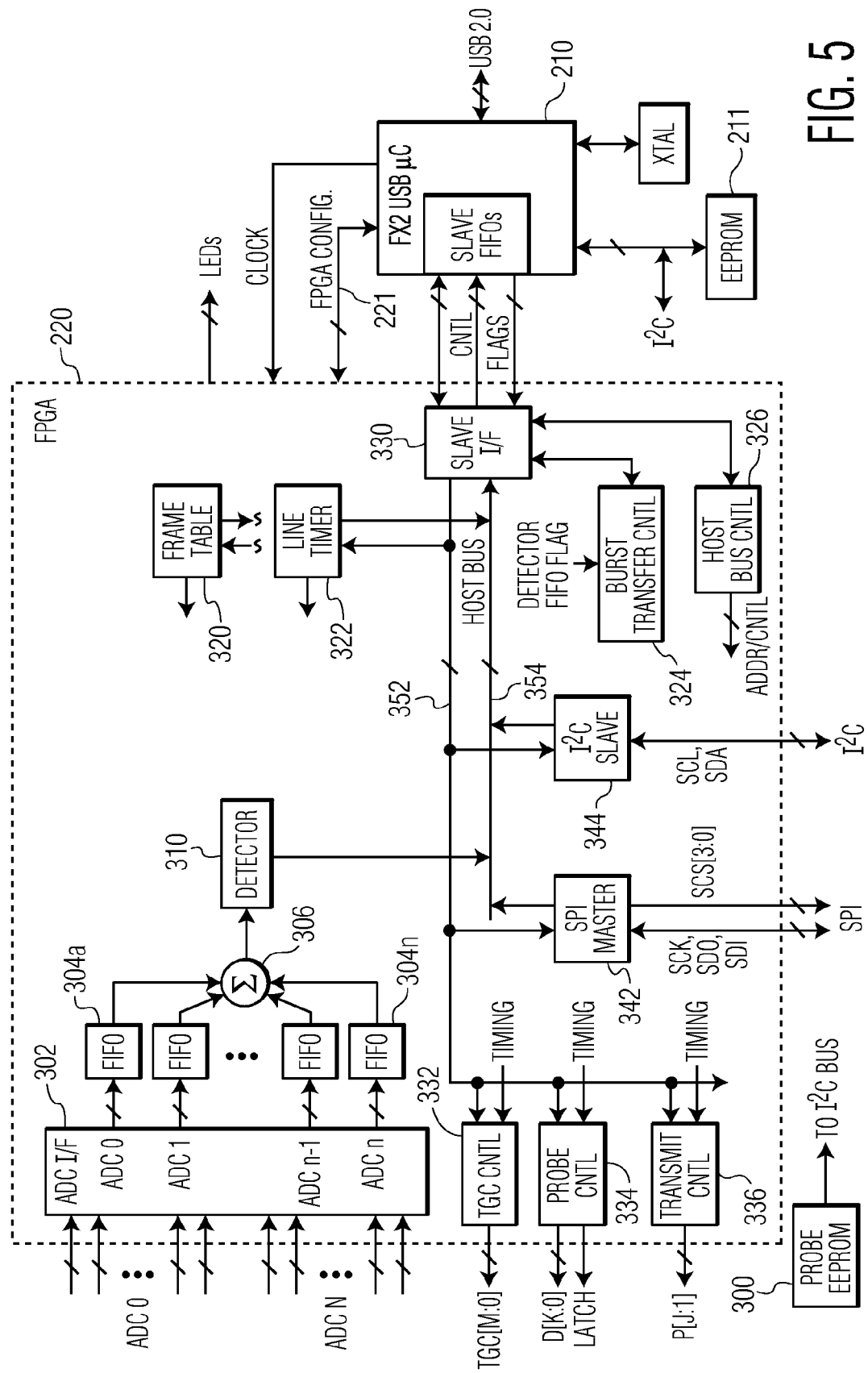
FIG. 5 illustrates the functions of a field programmable gate array which are configured by probe firmware in accordance with the principles of the present invention.

In a typical configuration the ultrasound signals received by dozens or hundreds of transducer elements in the probe are initially microbeamformed and combined down to a lesser number of ultrasound signal channels, such as eight, sixteen or thirty-two channels. The final beamforming of these eight, sixteen or thirty-two channels may be performed by the FPGA 220 which is programmed in this embodiment by firmware supplied by the probe for configuration as an eight-channel, sixteen-channel or thirty-two-channel receive beamformer as needed. The final beamformed line signals, which may also undergo other signal processing in the FPGA as described above, are coupled to the portable PC over the USB interface for image processing and display on the display 38 of the portable ultrasound system. An FPGA programmed by probe firmware in accordance with the principles of the present is shown in greater detail in FIG. 5. As previously mentioned, the FPGA may comprise components and modules such as logic gates, multiplexers, adders, counters, multipliers, memory devices, FIFOs and FIR filters which can be configured by firmware into a desired system configuration. In addition to functionality, power consumption may also be controlled by this process since the power consumed by the device will be a function of the components and modules connected and clocked for use in a given configuration. In the embodiment of FIG. 5 the firmware has defined a frame table 320 which defines an image frame to be acquired by the probe. The frame table in turn is coupled to the line timer 322 which defines the timing of each ultrasound line of the image frame. The frame table and line timer are coupled to buses 352 and 354 which are coupled to the slave interface 320 which interfaces with the USB microcontroller 210 to pass data to and from the portable ultrasound system processor. A host bus controller 326 facilitates these transfers. Two bus interfaces, a serial port interface 342 and an I$^2$C interface 344 enable transfers between the FPGA buses 352 and 354 and external data buses.

The operation of the probe in concert with the programmed FPGA is dictated by a probe controller 334. TGC data is transferred to the analog circuitry and the probe by a TGC controller 332. The timing of transmit events by the probe is controlled by a transmit controller 336. Echo signals from the probe and the ADCs 244 are interfaced to the FPGA circuitry by an ADC interface 302. The firmware from the probe determines the size of this interface depending upon the number of beamformer channels needed for the echo data received from the probe. Also determined by the firmware are the number of FIFOs 304a-304n used in the beamformer, one for each FPGA beamformer channel. The lengths and clock rates of the FIFOs are also determined by the firmware for the delay lengths needed to steer and focus echoes from the apertures of the probe. The delayed channel signals are summed by an adder arrangement 306 and the summed signals are detected by a detector 310 which is configured for the type of detection needed (e.g., amplitude detection or Doppler phase shift detection). The detected echo signals are transferred to the portable ultrasound system processor over the bus 354 and by the interface 330 under control of a burst transfer controller 324.

There are several ways to couple the firmware data from the storage device 300 of the probe, which in this embodiment is shown as an EEPROM. Alternatively the storage device can be a flash memory card such as the SD flash card. One way is by means of an I$^2$C bus coupled to the I$^2$C port on the FPGA which is coupled to the I$^2$C interface 344. The other is by means of an I$^2$C bus coupled to the USB microcontroller 210 to which an EEPROM 211 of data for the microcontroller 210 is coupled. The latter case, the firmware data is coupled from the microcontroller 210 to the FPGA over FPGA configuration lines 221. The probe firmware provides patterns of logical connections and states for programmable circuits in the FPGA 220, specifying configuration parameters such as the layout and operation of digital circuits in the FPGA and their interaction with external components. These circuits may be used for example to implement fast, efficient signal processing functions such as digital filtering and correlation. Typically FPGA configurations stored in the probe are contained in one of several industry standard formats such as ASCII "ttf" files.

Table 1 illustrates a number of ultrasound system functions which can be programmed by programmable hardware.

The portable ultrasound system 60 is controlled by a user interface such as that illustrated in concurrently filed U.S. patent application Ser. No. 11/911,119, entitled "PORTABLE ULTRASONIC DIAGNOSTIC IMAGING SYSTEM WITH DOCKING STATION." When the portable ultrasound system 60 is docked in the docking station 50, the probe may be connected to the analog module by a multiplexer between probe connector 56 on the docking station and the analog module by way of the docking connector between the docking station and the portable ultrasound system. When docked the ultrasound system is controlled by the control panel 44 with controls coupled to the docking connector and the ultrasound images are displayed on the docking station display 28.

It will be recognized that the concepts of the present invention can be used in other ways in an ultrasound system. For example, an FPGA and/or programmable analog circuitry can be used as an interface to probe circuitry in the probe and corresponding firmware data for the programmable device(s) can be stored in the ultrasound system rather than in the probe. When the probe is connected to the ultrasound system the firmware in the system is coupled to the probe to program an interface in the probe that is suitable for the ultrasound system which provided the firmware. In this embodiment a probe with a to-be-specified interface will have its interface defined by the ultrasound system to which it is connected, thereby enabling a probe to interface with a variety of different ultrasound systems. In a similar way configurable circuitry in the probe can be configured by firmware stored on the ultrasound system or in the probe connector.

TABLE 1

| Programmable Ultrasound System Hardware |
|---|
| DIGITAL PROGRAMMABLE HARDWARE (typically FPGA) |
| -Digital Beamformer |
|    -Transmit pulse generation: |
|       -delay resolution |
|       -aperture |
|    -Receive signal processing: |
|       -ADC sample rate |
|       -sub-sample interpolation: |
|          -averaging |
|          -digital filtering |
|       -total element group delay buffer depth |
|       -receive dynamic focus delay update engine |
|          -tables |
|          -algorithms |
| -Microbeamformer Download Controller |
|    -download clock: |
|       -set phase |
|       -duty cycle |
|       -frequency |
|    -microbeamformer coefficient format |
|    -coefficient data packing scheme |
| -Microbeamformer Operation |
|    -transmit and receive clocks: |
|       -phase |
|       -duty cycle |
|       -frequency |
|    -dynamic focus update signal generation |
| -Scan Control |
|    -frame generation (Frame Table) |
|    -line generation (Line Timer) |
| -Signal Processing |
|    -echo image detector |
|    -color flow detector |
|    -PW Doppler detector |
|    -special processing modes |
|    -contrast multi-line |
|    -splicing |
| -Scan conversion |
|    -display formats |
|    -interpolation |
| ANALOG PROGRAMMABLE HARDWARE |
|    Power Monitoring Circuits |
|    Thermistor Monitoring Circuits |
|    Receive Amplifier Configuration |
|    Variable Gain (TGC) Stage |
|    Harmonic Filters |
|    Anti-aliasing Filters |
|    CW Receive Processing |
|    Transmit Pulse Waveform Generator |

What is claimed is:

1. An ultrasound system, the system comprising:
an ultrasound probe which is removably connected to the ultrasound system and having a storage device comprising firmware data;
a connector by which the probe and the storage device are removably coupled to the ultrasound system; and
the ultrasound system having programmable circuitry comprising an FPGA coupled to the storage device and being configurable by the firmware data of the probe storage device.

2. The ultrasound system of claim 1, wherein the circuitry comprises at least one of programmable digital circuitry or programmable analog circuitry.

3. The ultrasound system of claim 2, wherein the programmable circuitry comprises programmable analog circuitry.

4. The ultrasound system of claim 1, wherein the storage device is located in the connector.

5. The ultrasound system of claim 1, wherein the probe further includes a microbeamformer located in the probe.

6. The ultrasound system of claim 1, wherein the firmware data comprises ttf files.

7. The ultrasound system of claim 1, wherein the programmable circuitry comprises signal processing circuitry.

8. The ultrasound system of claim 1, wherein the programmable circuitry comprises interface circuitry.

9. An ultrasound system including a display configured to present an image on the display, and the system further comprising:
an ultrasound probe having a storage device comprising firmware data;
a connector by which the probe and the storage device are removably coupled to the ultrasound system;
an ultrasound signal acquisition subsystem comprising an FPGA, located in the ultrasound system and responsive to the firmware data stored in the probe when the probe is connected to the ultrasound system, wherein the FPGA is configurable by the firmware data.

10. The ultrasound system of claim 9, wherein the FPGA includes digital beamformer circuitry which is configured by the firmware data stored in the probe.

11. The ultrasound system of claim 10, wherein the digital beamformer circuitry further comprises a receive beamformer.

12. The ultrasound system of claim 10, wherein the digital beamformer circuitry further comprises a transmit beamformer.

13. The ultrasound system of claim 9, wherein the ultrasound signal acquisition subsystem further includes programmable analog circuitry which is configured by the firmware stored in the probe.

14. The ultrasound system of claim 13, wherein the programmable analog circuitry further includes a programmable filter.

15. The ultrasound system of claim 13, wherein the programmable analog circuitry further includes a variable gain amplifier.

16. The ultrasound system of claim 9, wherein the ultrasound signal acquisition subsystem further comprises programmable analog circuitry and programmable digital circuitry which are responsive to the firmware stored in the probe.

17. The ultrasound system of claim 9, wherein the acquisition subsystem is configured at runtime.

* * * * *